United States Patent
Olson

(10) Patent No.: US 6,245,006 B1
(45) Date of Patent: Jun. 12, 2001

(54) MAGNET HOLDER

(75) Inventor: Allan M. Olson, Horsecreek, CA (US)

(73) Assignee: Orion Medical Group Inc., Sparks, NV (US)

( * ) Notice: Subject to any disclaimer, the term of this patent is extended or adjusted under 35 U.S.C. 154(b) by 0 days.

(21) Appl. No.: 09/375,737

(22) Filed: Aug. 17, 1999

(51) Int. Cl.$^7$ .................................................. A61B 17/52
(52) U.S. Cl. ................................................................ 600/15
(58) Field of Search ............................................ 600/9–15

(56) References Cited

U.S. PATENT DOCUMENTS

| | | | | |
|---|---|---|---|---|
| 4,656,068 | * | 4/1987 | Raines | ................................ 428/35 |
| 5,074,416 | * | 12/1991 | Hustad | ................................ 206/524.8 |
| 5,312,321 | | 5/1994 | Holcomb . | |
| 5,707,333 | * | 1/1998 | Bakst | ........................................ 600/9 |
| 5,803,260 | * | 9/1998 | Tilton | .................................... 206/463 |
| 5,813,971 | * | 9/1998 | Broderick | ................................ 600/15 |
| 5,849,378 | * | 12/1998 | Gask | .................................... 428/35.7 |
| 6,048,303 | * | 4/2000 | Porter | ...................................... 600/15 |

\* cited by examiner

*Primary Examiner*—Samuel G. Gilbert

(57) ABSTRACT

A permanent magnet assembly for use in a therapeutic product comprising four disk magnets held in an edge-to-edge array with a steel washer as an armature under the four magnets. The holder for the magnetic parts comprises two integrally joined sheets of flexible plastic such as PVC, one sheet constituting a body having indentations forming cavities sized and shaped for the magnetic parts, and the other sheet constituting a cover folded over and sealed to the body sheet around the indentations to hold the magnetic parts in place. Four alternative embodiments comprise single-magnet arrays with flat magnets of different shapes held in holders similar to the holder of the first embodiment but with cavities that are the same shapes as the single-magnet arrays.

10 Claims, 2 Drawing Sheets

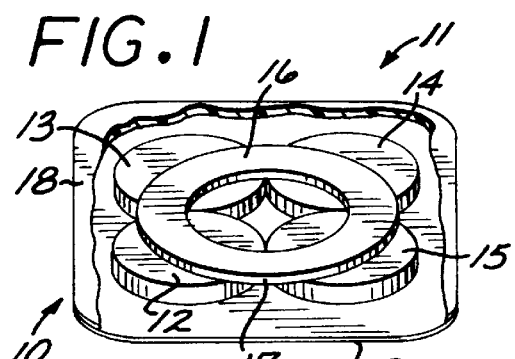
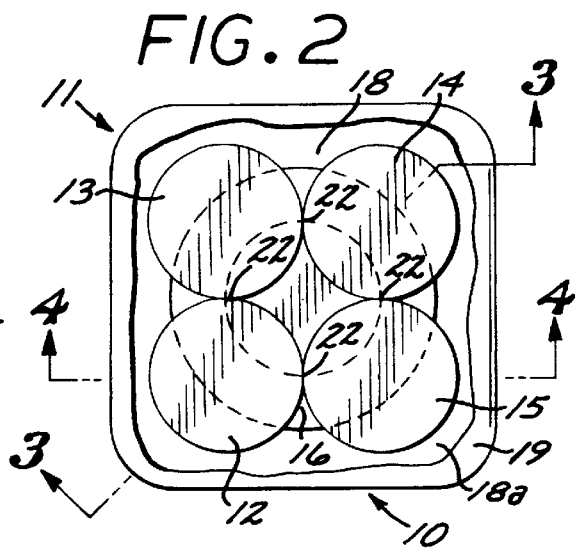
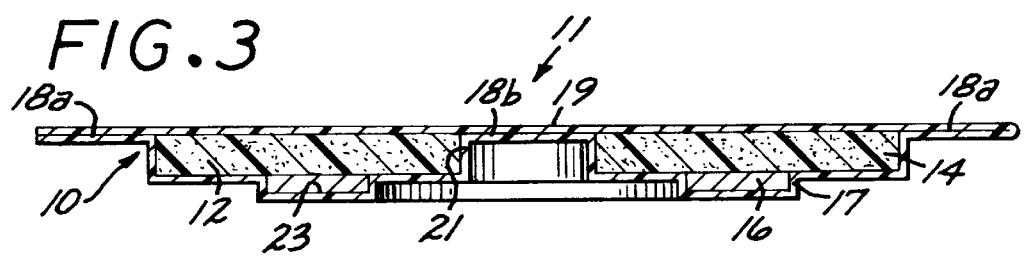
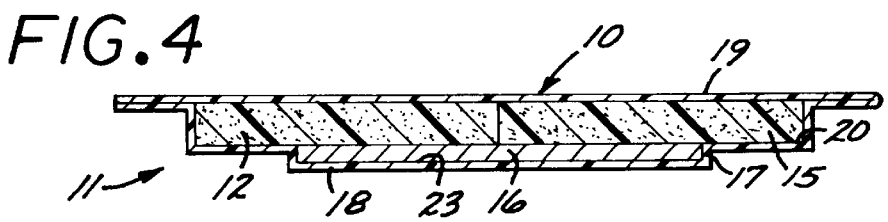
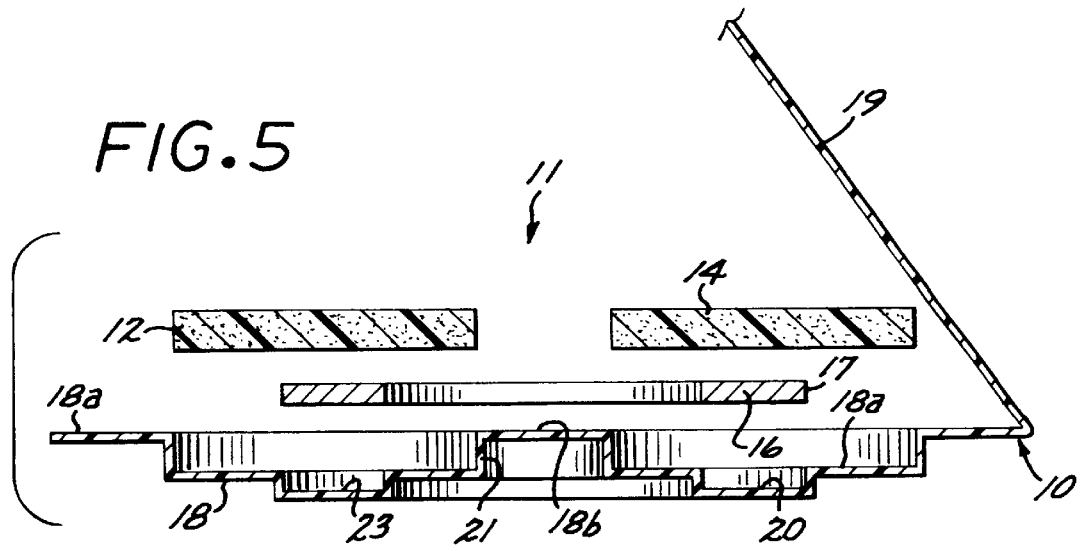

MAGNET HOLDER

BACKGROUND OF THE INVENTION

This invention relates to magnet assemblies, and has particular reference to the construction of magnet assemblies for application to the human body for therapeutic purposes.

There is growing support for the belief that magnetic therapy is an effective non-invasive, no-side-effects treatment that can speed recovery from a variety of conditions ranging from tendinitis and back pain to migraine headaches and a neuromuscular condition known as fibromyalgia. While the results of medical testing is regarded, at least by some, as inconclusive, many people believe, particularly in the alternative medicine field, that the application of one or more small, powerful magnets to the area of an injury will relieve pain and accelerate healing.

The use of therapeutic magnets has become popular among professional athletes, particularly golfers, and among a growing segment of the general population, even though there is a lack of a complete understanding of how they work. One view is that magnets affect pain receptors in the body, and one source claims that they suppress nerve cell action potentials by affecting the electrical potential across the cell membrane of a sensory neuron. This theory is stated in U.S. Pat. No. 5,312,321, which also discloses a magnet device for application to the body for therapeutic purposes. This device comprises generally a plurality of permanent magnets that are embedded in a mass of plastic material forming a flat containment body. This body permanently holds the magnets in a selected arrangement and orientation, believed to be important for generation of the desired magnetic field. A thin woven sheath also is suggested, but not shown, as a housing for the magnets.

The present invention is an improvement in the construction of the holder for a magnet assembly of the same general kind that is disclosed in the aforesaid patent, providing an improved magnet assembly that can be mass-produced economically in large numbers, and which is highly effective for its intended purpose. The holder effectively receives, positions and holds one or more permanent magnets of selected size and shape, preferably with an armature of ferrous material for enhancing the magnetic properties of the assembly, and houses the magnets in a manner that enhances the comfort of the user.

SUMMARY OF THE INVENTION

For the foregoing purposes, the magnet holder of the present invention comprises a flexible plastic body sheet having indentations in one of its sides defining cavities in the sheet corresponding in size and shape to the size and shape of the magnets to be held and the armature of the assembly, when an armature is to be included, and a flexible plastic cover sheet for overlying the indented side of the body sheet and covering the cavities after the pieces of the magnet assembly have been placed therein, the cover sheet being attachable to the body sheet around the cavities to complete the assembly.

In the preferred embodiment of the invention, the cover and body sheets are composed of the same material and are integrally joined together along corresponding sides, for folding of the cover sheet into its covering position and final attachment to the body sheet. The preferred flexible sheet material is plastic in which the indentations can be thermoformed and which can be heat-sealed together, and the indentations are in the form of a four-lobed upper cavity for holding four disk magnets immediately beneath the cover sheet and an annular cavity in the bottom wall of the cavity for holding the armature.

Other aspects and advantages of the invention will become apparent from the following detailed description, taken in conjunction with the accompanying drawings.

BRIEF DESCRIPTION OF THE DRAWINGS

FIG. 1 is a bottom perspective view of a magnet assembly incorporating a holder in accordance with the present invention, the body sheet of the holder being broken away and shown partially in cross-section for clarity;

FIG. 2 is a somewhat enlarged top plan view of the magnet assembly, with the cover sheet being broken away and shown partially in cross-section;

FIG. 3 is a further enlarged cross-sectional view taken substantially along line 3—3 of FIG. 2, and showing the full extent of the cover sheet and the body sheet;

FIG. 4 is a view similar to FIG. 3 but taken substantially along line 4—4 of FIG. 2;

FIG. 5 is an exploded view of the parts in FIG. 3, showing the cover sheet in a raised, open position;

DETAILED DESCRIPTION (FIGS. 1–5)

Figure 6:
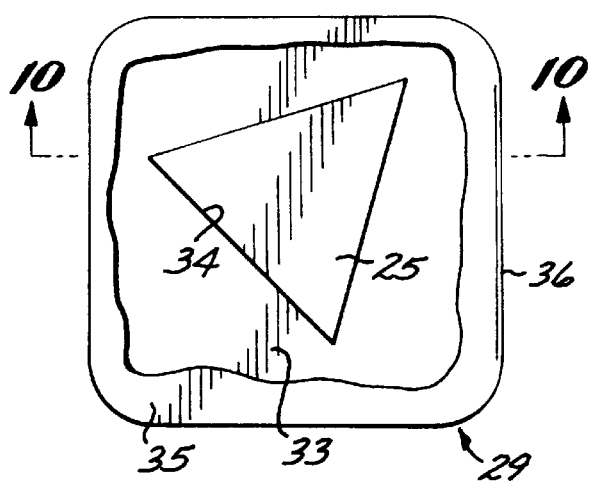
FIGS. 6, 7, 8 and 9 are top plan views similar to FIG. 2 and showing alternative illustrative embodiments of magnet assemblies with which a holder in accordance with the invention may be used, the magnets being, respectively, triangular, rectangular, circular and annular in shape.

As shown in the drawings for purposes of illustration, the invention is embodied in a holder 10 for a therapeutic magnet assembly, indicated generally by the reference number 11, comprising at least one permanent magnet, and herein an array of four permanent magnets 12, 13, 14, and 15 and an annular armature 16 positioned against one side of the array of magnets. The magnet assembly 10 is of the type that is intended to be sewn into a product, such as a wrist, head or knee band (not shown) by which it will be positioned and held against a part of the user's body to overlie an injury or a painful area. One or more magnet assemblies may be incorporated in a given product, depending upon size and design parameters, and variable numbers and sizes of magnets may be incorporated in a holder.

In the illustrative magnet assembly 10, the four magnets 12–15 are ceramic disk magnets of a well known and conventional type, which may vary in size from a small fraction of an inch to several inches in diameter. The illustrative magnets are arranged edge-to-edge in a flat array, with two disks 12 and 14 oriented in one direction (N poles up) and two 13 and 15 oriented in the opposite direction (S poles up). The armature 16, which is a steel washer, lies against one side of the array, the underside as viewed in FIGS. 2–4, and is sized to position its outer periphery 17 generally under the central portions of the disks. The armature is believed to have a beneficial effect of concentrating the magnetic field.

In accordance with the present invention, the holder 10 comprises two flexible plastic sheets 18 and 19, the first 18 constituting the body of the holder and being shaped with indentations forming cavities for receiving the magnetic parts, and the second 19 constituting the cover of the holder for overlying and closing the cavities to retain the magnetic parts in place. For rapid and economical manufacturing, the body and cover of the preferred embodiment are two integral portions of a single sheet of heat-shapable and heat-sealable material, such as polyvinylchloride ("PVC") film, so that the cover sheet 19 is foldable over and joinable to the body sheet 18 after the magnetic parts are in place.

As can be seen most clearly in FIGS. 2 and 5, the body sheet 18 herein has a generally flat top surface around its periphery (indicated at 18a) and generally in the center, indicated at 18b, and has a four-lobed relatively shallow cavity 20 (FIGS. 4 and 5) around the center surface 18b, which is the top of a post 21 that is centered in the four-lobed cavity 20. When the disks 12–15 are in this four-lobed cavity, they are held around the center 18b with their upper sides substantially level or "flush" with the top surfaces 18a and 18b and with their edges touching at four points 22, as shown in FIG. 2. In addition, the body sheet has a further indentation forming an annular cavity 23 in the bottom of the cavity 20, surrounding the center post 21 for receiving the annular armature 16 and holding it against the undersides of the four disks 12–15. The relationship of these parts is shown most clearly in FIGS. 1 and 2.

While the holders may be made in any desired shape, rectangular is a preferred shape for ease of manufacture and handling. For mass production, a plurality of holders may be pre-formed in a single large sheet (not shown) of PVC and then punched or cut out as individual elongated rectangular sheets having the body sheets 18 constituting one end portion and the cover sheets 19 integrally joined to the body sheets, as foldable flaps, and constituting the opposite end portions of the elongated sheets. For example, twenty-four holders may be pre-formed in a single sheet, in four rows of six each, and then separated from the single sheet into twenty-four individual holders.

Then an armature 16 is placed in the armature cavity 23 of the holder 10, as shown in FIG. 5, and four magnet disks 12–15 of the proper size and shape are placed in the magnet cavity 20 over the armature, and the cover sheet 19 is bent over to form a fold at 24, at the approximate longitudinal midpoint of the elongated sheet to form a neatly covered holder. Finally, the cover and body sheets are joined together, which may be accomplished quickly and effectively by heat sealing at the surfaces 18a and 18b of the body sheet, joining it securely to the underside of the cover sheet. With the body sheet and cover sheet joined in this way, the magnetic parts 12–16 are held securely in their proper positions.

DESCRIPTION OF THE ALTERNATIVE EMBODIMENTS

Figure 7:
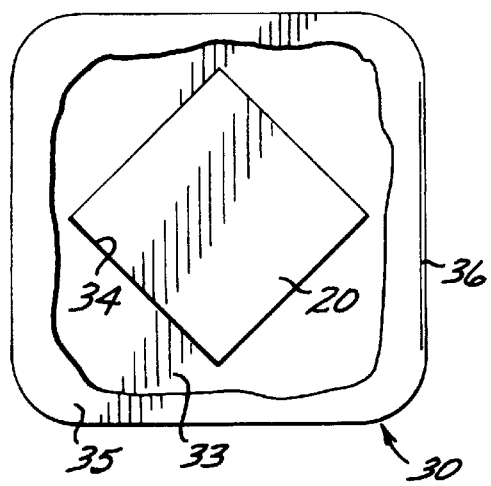
Figure 8:
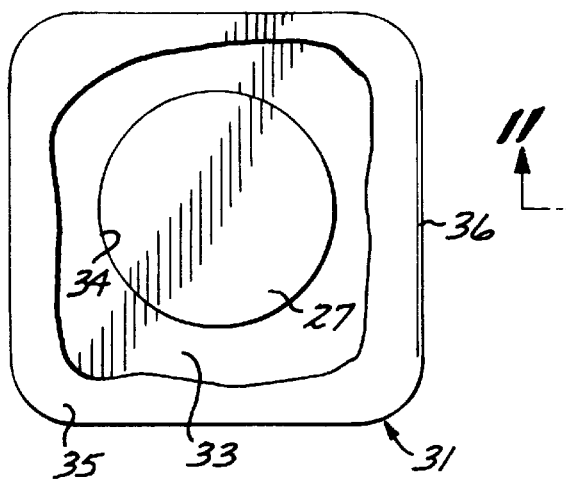
Figure 9:
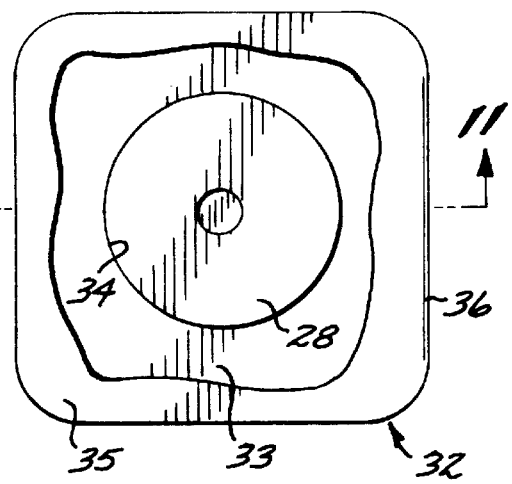
Figure 10:
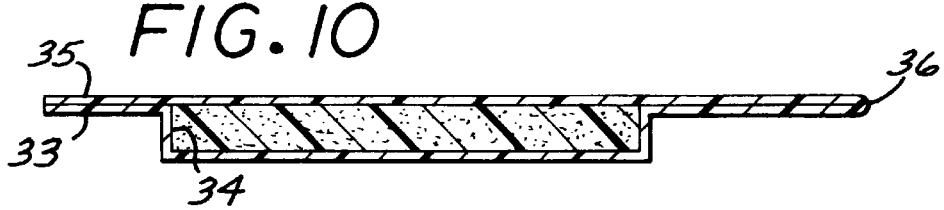
FIG. 10 is a somewhat enlarged cross-sectional view taken along line 10—10 of FIG. 6.
Figure 11:
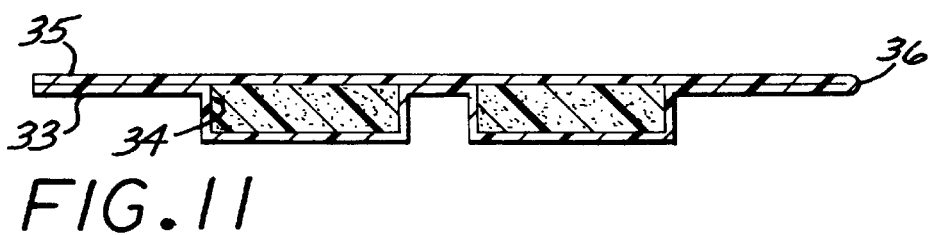
FIG. 11 is a view similar to FIG. 10 taken along line 11—11 of FIG. 9.

Shown in FIGS. 6 through 11 are four alternative embodiments showing four different shapes of permanent magnets 25, 26, 27 and 28 that are triangular, square, circular and annular, respectively. These magnets are packaged in holders 29, 30, 31 and 32, respectively, in accordance with the present invention. While only one permanent magnet is shown in each of these holders, constituting a single-magnet array, it is to be understood that a plurality of such magnets may be included, as desired.

In each of these embodiments, a body sheet 33 is formed with an indentation forming a cavity 34 that is shaped to receive and position the associated magnet, and a cover sheet 35 overlies the body sheet to close the cavity. The cover sheets are integrally joined to the body sheets by folds 36, and are joined to the body sheets around the cavities to secure the magnets in place. No armatures are shown, but the cavities will be shaped appropriately if a plurality of magnets and an armature are to be included in the holder.

From the foregoing, it will be seen that the present invention provides a simple, inexpensive and effective holder for permanent magnet assemblies that may be mass produced economically and that are usable in a comfortable and convenient fashion in products designed for magnetic therapy. It also will be evident that various modifications and changes may be made without departing from the spirit and scope of the invention.

I claim as my invention:

1. In a magnet assembly including an array of disk-shaped permanent magnets having flat sides and narrow edges and arranged in edge-to-edge relation, and an armature disposed against said array in contact with corresponding flat sides of said magnets, a sealed, flexible magnet holder, comprising:

a first sheet of flexible plastic having a first indentation defining a plurality of side-by-side first cavities in one side of the sheet, said cavities being of substantially the same size and shape as said magnets and receiving and holding the magnets in the edge-to-edge array;

said first sheet having a further indentation in said first indentation defining a second cavity underlying said first cavities, said second cavity being of substantially the same size and shape as the armature and holding the latter under and against the magnets;

a second sheet of flexible plastic overlying said first sheet and covering said cavities, said sheets being opposite end portions of a single elongated sheet and joined together by an integral fold;

and means sealing said first and second sheets together around said first indentation thereby to hold the magnet array in sealed, assembled relation.

2. A holder as defined in claim 1 wherein said first sheet has thermoformed indentations forming said cavities.

3. A holder as defined in claim 1 wherein said flexible plastic is PVC.

4. A holder as defined in claim 1 wherein said indentation defines four lobe-shaped cavities arranged around a central post, and said sheets have flat engaging surfaces sealed together around said cavities.

5. A holder as defined in claim 1 wherein the armature and said second cavity are annular in shape.

6. A holder as defined in claim 1 wherein said first and second sheets are generally rectangular in shape.

7. For use in combination with a permanent magnet array, a flexible holder for the array adapted to be sealed in water-tight relation around the array for use in a therapeutic product, said holder comprising:

first and second flexible plastic sheets composed of heat-sealable material constituting a body sheet and a cover sheet, respectively;

said body sheet having at least one indentation forming a cavity for receiving the magnet array and holding the array in a selected position relative to the body sheet, said cover sheet overlying the indentation and covering the cavity;

said sheets having flat opposing surfaces extending around the indentation to be heat-sealed together after the magnet array is placed in the cavity.

8. A holder as defined in claim 7 wherein said holder is for use with a magnet array that constitutes at least one flat magnet of preselected size and shape, and the indentation has the same size and shape as the array.

9. A holder as defined in claim 7 wherein said holder is for use with a magnet array that has a preselected number of magnets of a preselected size and shape arranged in flat edge-to-edge relation, and said indentation defines said preselected number of cavities of substantially the same preselected size and shape in edge-to-edge relation, said cover sheet overlying the body sheet and covering said cavities to seal the cavities when the sheets are heat-sealed after a magnet array is placed in the cavities.

10. A holder as defined in claim 7 wherein said body and cover sheets are the opposite end portions of a single elongated flexible sheet and are integrally joined together by a fold.

* * * * *